United States Patent

Kim

Patent Number: 5,904,664
Date of Patent: May 18, 1999

[54] MUGWORT MOXACAUTERY DEVICE

[76] Inventor: Jin Sup Kim, 152-11, Kyo Hyun-Ri, Jang Jeung-Myun, Yang Ju-Kun, Kyung Ki-do, Rep. of Korea, 482-810

[21] Appl. No.: 08/983,039

[22] PCT Filed: May 17, 1997

[86] PCT No.: PCT/KR97/00087

§ 371 Date: Jan. 15, 1998

§ 102(e) Date: Jan. 15, 1998

[87] PCT Pub. No.: WO97/44087

PCT Pub. Date: Nov. 27, 1997

[30] Foreign Application Priority Data

May 18, 1996 [KR] Rep. of Korea .................. 1996/16843
May 15, 1997 [KR] Rep. of Korea .................. 1997/18707

[51] Int. Cl.$^6$ ............................ A61N 1/30; A61M 37/00; A61F 7/00
[52] U.S. Cl. ................................ 604/19; 604/24; 604/291
[58] Field of Search .................................. 604/19, 23, 24, 604/291; 607/113, 96; 126/15 A, 204; 424/409

[56] References Cited

U.S. PATENT DOCUMENTS

| | | | |
|---|---|---|---|
| 4,203,438 | 5/1980 | Shiu | 128/254 |
| 4,325,371 | 4/1982 | Atsumi | 128/254 |
| 4,671,788 | 6/1987 | Wu | 604/24 |
| 4,731,050 | 3/1988 | Harada et al. | 604/24 |
| 4,747,841 | 5/1988 | Kuratomi et al. | 604/291 |
| 5,043,280 | 8/1991 | Fischer et al. | 435/235.1 |

*Primary Examiner*—Wynn Wood Coggins
*Assistant Examiner*—Michael J. Hayes
*Attorney, Agent, or Firm*—Jacobson, Price, Holman & Stern, PLLC

[57] ABSTRACT

A mugwort moxacautery device in which herbal ingredients plus medicinal mugwort composition may be deeply permeated into the affected area of skin by fumigating them based on combustion efficiency of the mugwort pole and its combustion heat. The moxacautery device (4) with aromatic herbal medicines has a lower body (1), upper body (2) and lid (3) in earthen ware. An herbal-medicine ring (7) and porous plate for herbal medicine (6) are mounted to the center-empty portions (8, 9) in a lower body (1) and upper body (2) in a sequential order. A mugwort pole (5) is provided between the inside of upper body (2) and netting plates (10, 11) are placed between the upper body (2) and lid (3).

4 Claims, 3 Drawing Sheets

MUGWORT MOXACAUTERY DEVICE

FIELD OF THE INVENTION

This invention relates to a mugwort moxacautery device and in particular, to a mugwort moxacautery device in which some herbal ingredients contained in a porous plate for herbal medicine and herbal-medicine ring can be deeply permeated into the skin in the midst of a safely-burnt mugwort pole in the moxacautery device and a combustion heat of mugwort pole, thus guaranteeing the safety and remarkable therapeutic effects of the mugwort moxacautery device.

DESCRIPTION OF THE RELATED ART

Conventional mugwort moxacautery devices have a structure to simply manufacture of a mugwort pole for combustion use by compressing the medicinal mugwort fibroid materials. However, these devices have several shortcomings in that a) insufficient oxygen supply around the mugwort pole has failed to gain perfect combustion effects, thus resulting in poor combustion, b) when the mugwort pole is burnt, large amounts of smoke occur and there remains high risk of skin burns owing to excessive heat of combustion during use, and c) poor permeation of the mugwort pole via the skin has not produced satisfactory therapeutic effects.

SUMMARY OF THE INVENTION

To overcome the aforementioned shortcomings that the convention devices face, an object of this invention is to provide a mugwort moxacautery device with greater safety and having remarkable therapeutic effects. The device is formulated in such a structure that a porous plate for herbal medicine and herbal ingredients of herbal-medicine ring are deeply permeated into the skin with a combustion heat, being burnt in the upper part of moxacautery device, while avoiding excessive heat with a skin directly, Another object of this invention is to provide a mugwort moxacautery device with more safe and remarkable therapeutic effects comprising:

a combustion cup, having appropriate intervals with the side of mugwort pole and thus helping combustion of the mugwort pole, is installed in the upper body of moxacautery device; and a lower body itself, being combined with the upper body, is formed in such a manner to contain some active ingredients such as ginger, garlic and mugwort in powder form; and the lower body of moxacautery device is inletted to the upper body within a casing made of silicone rubber or paper so that a medicinal mugwort composition of mugwort pole and herbal medicine composition of lower body are deeply permeated into the skin, in addition to stable formulation of said moxacautery device; and effective prevention of skin burns associated with heat of moxacautery device during mugwort moxacautery may be available.

BRIEF DESCRIPTION OF THE DRAWINGS

This invention is explained in more detail as set forth hereunder by referring to the attached drawings.

DETAILED DESCRIPTION OF THE PREFERRED EMBODIMENT

Figure 1:
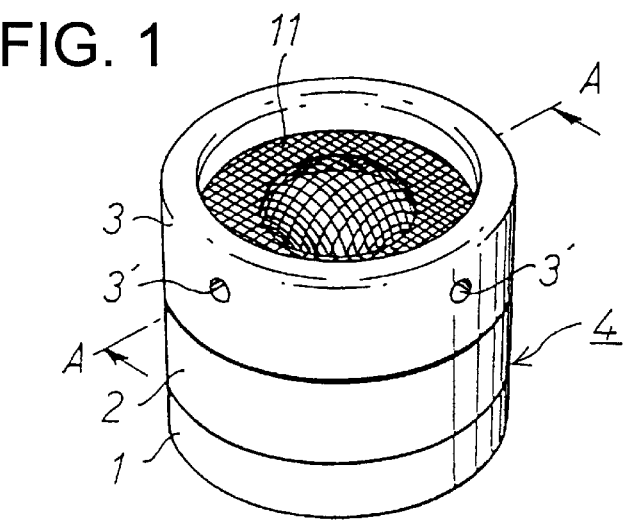
FIG. 1 is a perspective view of one example of mugwort moxacautery device according to this invention.
Figure 2:
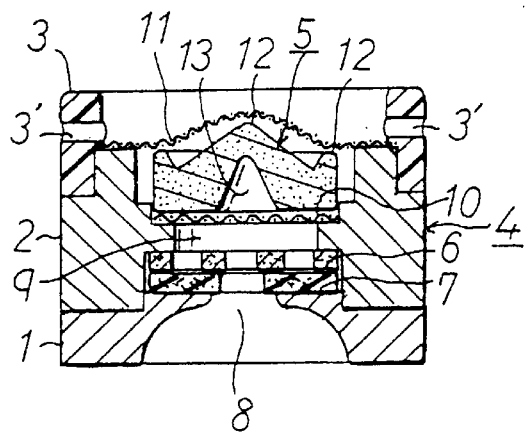
FIG. 2 is a cross-section taken along line A—A of FIG. 1.
Figure 3:
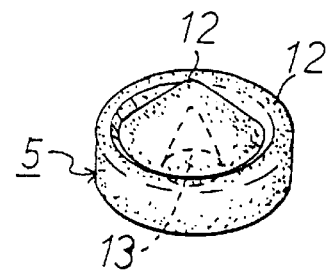
FIG. 3 is a perspective view of a mugwort pole.
Figure 4:
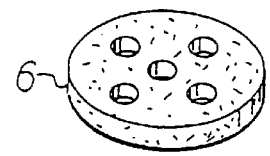
FIG. 4 is a perspective view of a porous plate.
Figure 5:
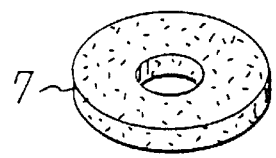
FIG. 5 is a perspective view of an herbal medicine ring.

As revealed in FIGS. 1 and 2, the moxacautery device (4) consists of lower body (1), upper body (2) and lid (3), and of mugwort pole (5) and porous plate for herbal medicine (6) and herbal-medicine ring (7) installed into the moxacautery device (4), as shown in FIGS. 3, 4 and 5. An extended nozzle-type of center-empty portion (8) is formed at the center of lower body (1); a center-empty portion (9) is formed at the center of upper body (2) inletted with said lower body (1); a porous plate for herbal medicine (6) and herbal-medicine ring (7) are inserted between the upper part of said center-empty portion (9) and lower body (1); a first netting plate (10) is placed on the upper part of said center-empty portion (9); a mugwort pole (5) is inserted on the netting plate (10); the mugwort pole (5) may be protected in such manner that it is placed in the lower part of a second netting plate (11) fixed by lid (3), which is inletted on the upper body (2).

The lid (3) is in the form of ring and several air holes (3') are formed at its side wall.

From a moxacautery device (4) according to this invention, the upper and lower bodies (1, 2) are constructed in such a manner that a yellow soil of good quality is diluted to water and foreign materials such as sand are removed. After settling the sediments, the mixture is separated from water and dried to be in powder state. Then, to facilitate the absorption of a medicinal mugwort composition contained in the mugwort pole (5) as well as herbal ingredients contained in porous plate for herbal medicine and herbal-medicine ring (7) into the human body, an aromatic herbal medicine and adhesive are mixed with said powder with addition of water to manufacture a granule form. Then, said granule form is pressurized and compressed in a mold, dried and grounded for manufacturing said upper and lower bodies.

The porous plate for herbal medicine (6) and herbal-medicine ring (7) are constructed in such a manner that after mixing and kneading with starches such as herbal medicine in powder form, the mixture is molded in a mold or imprinted with a porous plate, and followed by a drying process.

The mugwort pole (5) is constructed in such a manner that a medicinal mugwort in powder form is purified by a sieve to obtain about 30% pure mugwort fibroid material; then, said pure material is mixed with bioceramics with appropriate addition of water, kneaded, and compressed in a mold under high pressure.

Namely, as illustrated in FIGS. 2 and 3, a protracted portion (12) for efficient ignition is formed at the brim and center of mugwort pole (5), while an inlet (13) for efficient oxygen supply is formed at the lower center.

In particular, since the mugwort pole (5) itself has a microporous structure, perfect combustion may be guaranteed even with small amount of oxygen supplied.

Figure 6:
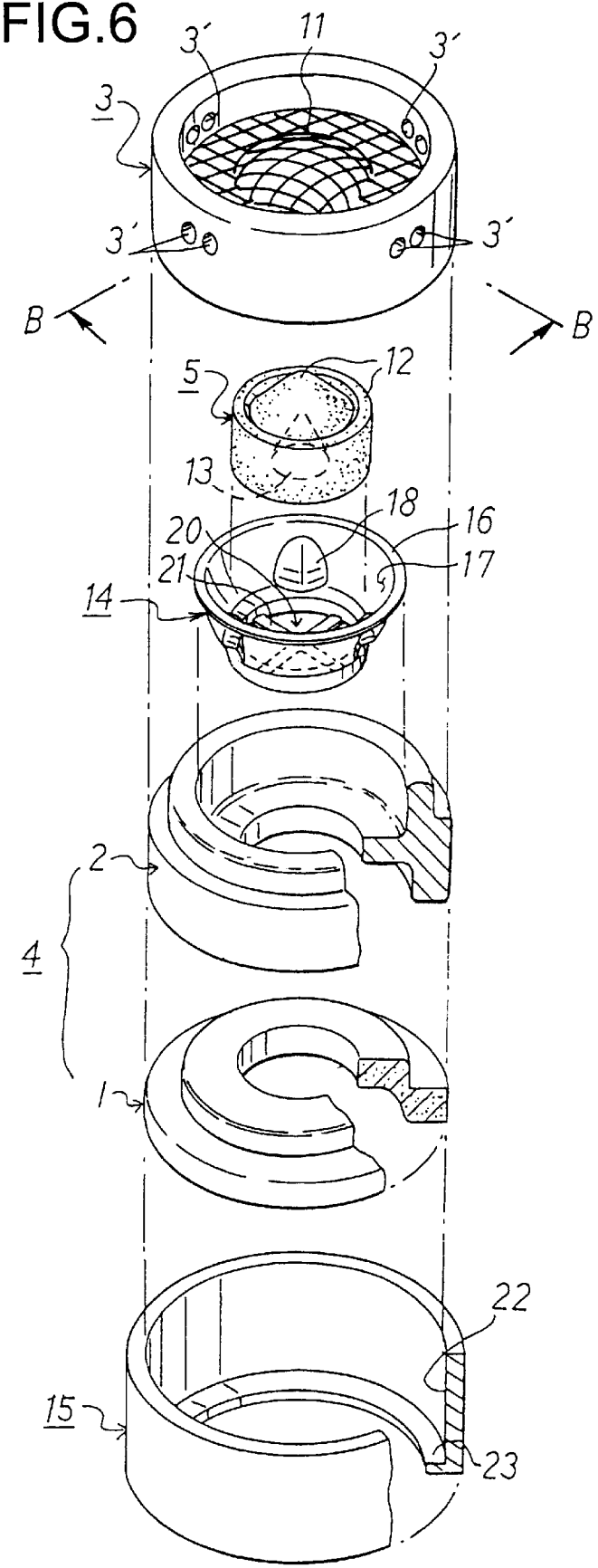
FIG. 6 is an exploded view of a second embodiment of the mugwort moxacautery device.
Figure 7:
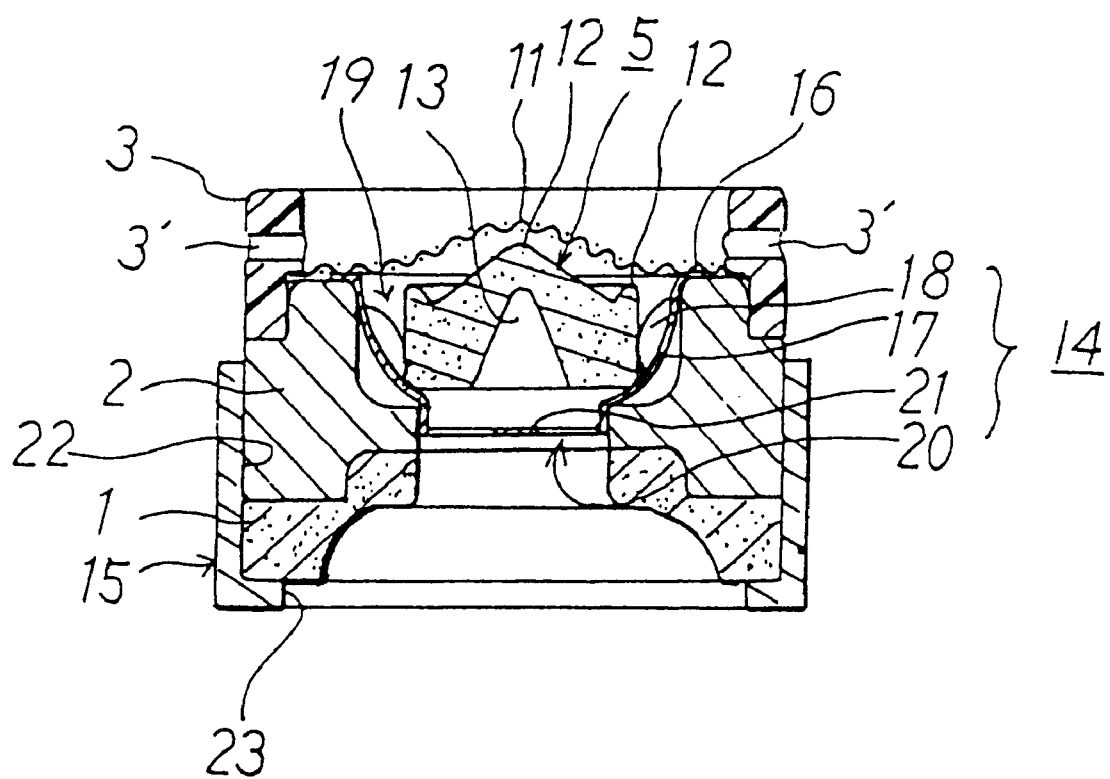
FIG. 7 is a cross-section taken along line B—B of FIG. 6.

Another example of a mugwort moxacautery device according to this invention is illustrated in FIGS. 6 and 7.

A combustion cup (14), being inserted with a mugwort pole (5), is installed in the upper body (2) of moxacautery device (4). The lower body (1) itself is constructed in such manner to contain some active ingredients such as ginger, garlic and mugwort in powder form. Said lower body (1) and upper body (2) are inletted into a casing (15) made of silicone rubber or caper in sequential order.

A combustion cup (14) is made of metal; at the upper part, a flange (16) is formed so as to be placed on the upper body (2) of moxacautery device (4); from the inside of side wall (17) having larger diameter than mugwort pole (5), several protracted portions (18) inletted with the mugwort pole (5) are formed so that a space portion (19) between the side wall (17) and mugwort pole (5) may be safeguarded; to a center-empty portion (20) at very lower part, a pad (21) across the center-empty portion (20) is formed horizontally.

A casing (15) is constructed in such a manner that the side wall (22) is wider than the lower body (1) and upper body (2) of said moxacautery device (4) in sequential order. A cycled keeper (23) is formed at a side wall (22) is formed inwardly in order for the lower body (1) not to be deviated downwardly. Thus, the casing 15 can receive the lower body, the upper body 2 with combustion cup 14, and mugwort pole 5.

The mugwort moxacautery device so constructed as above, is formulated for use, as illustrated in FIG. 7.

When a mugwort pole (5) is placed on the combustion cup (14), a space portion (19) between the side wall (17) of combustion cup (14) and mugwort pole (5) is safeguarded so that the mugwort pole (5) is well burnt. Also, when the mugwort pole (5) is burnt between the pad (21) at the center-empty portion (20) supporting the mugwort pole (5), resinous solution of medicinal mugwort, so formed, is well permeated into the affected area of skin.

Further, since the lower body (1) of moxacautery device (4) is constructed in such a manner to contain some active ingredients such as ginger, garlic and mugwort in powder form, herbal ingredients of mug-wort pole (5) contained in the lower body (1) plus a medicinal mugwort composition are permeated into the affected area of skin by a heat of mugwort pole (5).

Further, since a lower body (1) and upper body (2) of said moxacautery device (4) is formulated in piled form within the casing (15) made of silicone rubber or paper, the formulation of said moxacautery device (4) is maintained in very stable state and remarkable heat-screening effects between heated moxacautery device (4) and affected skin area may prevent any possible skin burns during mugwort moxacautery.

The effects of this invention, so constructed as above, are described as follows:

As shown in FIG. 2, this invention is characterized in that a porous plate for herbal medicine (6) and herbal-medicine ring (7) are mounted to the center-empty portion (8, 9) of lower body (1) and upper body (2) in earthen ware having aromatic herbal medicines added; the mugwort pole (5), protected by a first netting plate (10) fixed by a upper body (2) and a second netting plate (11) fixed between a lid (3) and upper body (2), is installed to the upper part of a porous plate for herbal medicine (6). Therefore, when the mugwort pole (5) is ignited by placing a moxacautery device (4) on the affected area of skin, the ignition of mugwort pole (5) is easily available since protracted portion (18) is provided on its upper part. At the same time, since the mugwort pole (5) has an inlet (13) at the lower part, combustion is easily and perfectly available since staying space of oxygen, i.e., contact area with air is enlarged, even with small amounts of oxygen supplied.

In particular, since the mugwort pole (5) has a microporous structure, combustion is further available. Since the heat, generated from the combustion of mugwort pole (5), is lowered by a porous plate for herbal medicine (6) and herbal-medicine ring (7) at a bottom of the mugwort pole (5), there is no risks of any skin burns. Also, owing to combustion heat of the mugwort pole (5), the herbal ingredients contained in both the porous plate for herbal medicine (6) and herbal-medicine ring (7) are fumigated and deeply permeated into skin, together with a medicinal mugwort composition of the mugwort pole (5).

In addition, since some aromatic herbal medicines are added to the moxacautery device (4) of this invention having a lower body (1) and upper body (2) so as to potentiate the permeating effects of both fumigated medicinal mugwort composition and herbal ingredients, their permeating effects prove to be remarkable and the moxacautery device (4) is quite safe in that the perfect combustion of mugwort pole is guaranteed so that there is no risks of any skin burns, when treated. Since the mugwort pole (5) is covered with the second netting plate (11), there is no risks of any skin burns, when treated.

Further the mugwort moxacautery device according to this invention, as illustrated in FIGS. 6 and 7, has several advantages in that a) with a combustion cup provided herein, the combustion efficiency of mugwort pole (5) is enhanced so as to ensure the perfect combustion of mugwort pole (5), b) since the lower body (1) contains herbal ingredients therapeutic effects may be obtained by permeating the herbal ingredients into the affected area of skin without separate use of porous plate or herbal-medicine ring, c) since the moxacautery device (4) consisting of lower body (1) and upper body (2) is inletted to a casing (15) made of silicone rubber or paper, there is no risk that the formulation of moxacautery device (4) get scattered during use, and d) even though the moxacautery device (4) during mugwort moxacautery is heated, the heat is not directly delivered to a skin, thus preventing any possible occurrence of burns.

Also, when the lower body (1) and upper body (2) are inletted of moxacautery device (4) in casing (15), an end-user is in the position to optionally modulate the distance between a lower body (1) and upper body (2), within allowable heights of the casing (15); namely, the distance between the mugwort pole (5) and affected area of skin.

What is claimed is:

1. A mugwort moxacautery device comprising:
   a lower body;
   an upper body;
   a lid;
   an herbal-medicine ring and a porous plate, the herbal-medicine ring and porous plate each mounted in a central opening formed between the lower body and the upper body; and
   a mugwort pole positioned between a first netting plate formed at the upper body and a second netting plate formed at the lid.

2. The device set forth in claim 1, wherein the lower and upper bodies are formed in a mold, and are made of aromatic herbal medicines.

3. A mugwort moxacautery device as set forth in claim 1, wherein the mugwort pole has a protracted portion for ignition formed at an upper brim and at a center of the mugwort pole, and a combustion-facilitating inlet formed at an upper center of the mugwort pole.

4. A mugwort moxacautery device comprising:
   a lower body;
   an upper body;
   a lid;
   a combustion cup that is received into the upper body, the combustion cup including a pad on which a mugwort pole is placed, a side wall having protracted portions formed inwardly from the side wall of said combustion cup to receive the mugwort pole, the protracted portions forming a space between the side wall and the mugwort pole, and a flange laid on the upper body; and
   a casing receiving the lower and upper bodies, the casing including a side wall and a projection extending inwardly from a lower portion of the side wall of the casing.

\* \* \* \* \*